(12) United States Patent
Tan (10) Patent No.: US 6,461,851 B1
(45) Date of Patent: *Oct. 8, 2002

(54) HIGH EXPRESSION MODULES CONTAINING TWO OR MORE TANDEM COPIES OF A METHIONINASE ENCODING SEQUENCE

(75) Inventor: Yuying Tan, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/479,275

(22) Filed: Jan. 5, 2000

Related U.S. Application Data (63) Continuation of application No. 08/908,860, filed on Aug. 8, 1997, now abandoned, which is a continuation-in-part of application No. 08/642,541, filed on May 3, 1996, now Pat. No. 5,891,704, which is a continuation-in-part of application No. 08/486,519, filed on Jun. 5, 1995, now Pat. No. 5,715,835, which is a continuation-in-part of application No. 08/424,300, filed as application No. PCT/US93/11311 on Apr. 24, 1995, now Pat. No. 5,690,929, which is a continuation-in-part of application No. 07/979,165, filed on Nov. 19, 1992, now abandoned.

(51) Int. Cl.$^7$ ................................................. C12N 9/88
(52) U.S. Cl. ............... 435/232; 435/252.33; 435/320.1; 536/23.2
(58) Field of Search ................................ 435/232, 325, 435/252.3, 252.33, 320.1; 536/23.2

(56) References Cited

U.S. PATENT DOCUMENTS

| | | | |
|---|---|---|---|
| 4,071,405 A | 1/1978 | Soda et al. | 195/29 |
| 4,298,590 A | 11/1981 | Bogoch | 424/1 |
| 4,952,496 A | 8/1990 | Studier et al. | 435/91 |
| 5,028,420 A | 7/1991 | Masegi | 424/85.1 |
| 5,077,211 A | 12/1991 | Yarosh | 435/193 |
| 5,487,984 A | 1/1996 | Allet et al. | 435/69.5 |
| 5,571,510 A | 11/1996 | Nobori et al. | 424/94.5 |

FOREIGN PATENT DOCUMENTS

| | | |
|---|---|---|
| JP | 53052682 | 5/1978 |
| WO | WO 94 11535 | 5/1994 |
| WO | WO 96 40284 | 12/1996 |

OTHER PUBLICATIONS

Breillout et al., "Methionine Dependency of Malignant Tumors: A Possible Approach for Therapy," *J Natl Cancer Inst* (1990) 82:1628–1632 and 1593–1660.
Carr et al., "Isolation and Characterization of Bacterial L–Methioninase as an Effective Antitumor Agent," *Bios* (1981) 52(1): 13–22.
Chello et al., "Dependence of 5–Methyltetrahydrofolate Utilization by L5178Y Murine Leukemia Cells In Vitro on the Presence of Hydroxycobalamin and Transcobalamin II," *Cancer Res* (1973) 33:1898–1904.
Cohen et al., "Nonchromosomal Antibiotic Resistance in Bacteria: Genetic Transformation of *Escherichia coli* by R–Factor DNA," *Proc Natl Acad Sci USA* (1972) 69:2110–2114.
Database WPI, Section Ch, Week 7825, Derwent Publications Ltd. (Mitsui Toatsu Chem., Inc.), AN 78–44945A, JP 53–52682 A (May 13, 1978).
Database WPI, Section Ch, Week 9738, Derwent Publications Ltd. (Shionogi & Co. Ltd.), AN 97–409889, JP 09182592 A (Jul. 15, 1997).
Dethy et al., "Carbon–11–Methionine and Fluorine–18–FDG PET Study in Brian Hematoma," *J Nuclear Med* (1994) 35:1162–1166.
Eagle, "Nutrition Needs of Mammalian Cells in Tissue Culture," *Science* (1955) 122:501–504.
Eagle, "Amino Acid Metabolism in Mammalian Cell Cultures," *Science* (1959) 130:432–437.
Ford et al., "Fusion Tails for the Recovery and Purification of Recombinant Proteins," *Protein Expression and Purification* (Apr./Jun. 1991) 2(2/3):95–107.
Freeman et al., "In Vivo–Like Growth of Human Tumors In Vitro," *Proc Natl Acad Sci USA* (1986) 83:2694–2698.
Goseki et al., "Antitumor Effect of Methionine–Depleting Total Parenteral Nutrition with Doxorubicin Administration on Yoshida Sarcoma–Bearing Rats," *Cancer* (1992) 69:1865–1872.
Graham et al., "A New Technique for the Assay of Infectivity of Human Adenoviruss 5 DNA," *Virology* (1973) 52:456–467.
Hernandez et al., "Los Liposomas, Entre Modelo de Membranas Biologicas Y Transportadores de Principios Activos," *Cir Farm* (1987) 293:49–60.
Hoffman et al., "Reversible Growth Arrest in Simian Virus 40–Transformed Human Fibroblasts," *Proc Natl Acad Sci USA* (1980) 77:7306–7310.
Hoffman et al., "A General Native–State Method for Determination of Proliferation Capacity of Human Normal and Tumor Tissues In Vitro," *Proc Natl Acad Sci USA* (1989) 86:2013–2017.
Hoffman et al., "Altered Methionine Metabolism, DNA Methylation and Oncogene Expression in Carcinogenesis," *Biochem Biophys Acta* (1984) 738:49–87.
Hoffman, et al., "Altered Methionine Metabolism and Transmethylation in Cancer," *Anticancer Res* (1985) 5:1–30.
Huovinen et al., "Carbon–11–Methionine and PET in Evaluation of Treatment Response of Breast Cancer," *Br J Cancer* (1993) 67:787–791.

(List continued on next page.)

Primary Examiner—Nashaat T. Nashed
(74) Attorney, Agent, or Firm—Morrison & Foerster LLP (57) ABSTRACT

The construction of multicopy expression systems for methioninase are disclosed. The higher expression systems employ a promoter operably linked to two or more copies of a tandemly repeated methioninase encoding sequence. Such multicopy expression systems were found to produce unexpectedly high levels of methioninase when expressed in an appropriate host.

5 Claims, 7 Drawing Sheets

OTHER PUBLICATIONS

Inoue et al., "Structural Analysis of the L–Methionine Gamma–Lyase Gene from Pseudomonas Putida," *Journal of Biochemistry* (1995) 117(5):1120–1125.

Ito et al., "Purification and Characterization of Methioninase from *Pseudomonas putida*," *J Biochem* (1976) 79:1263–1272.

Kang, "Hyperhomocyst(e)inemia as a Risk Factor for Occlusive Vascular Disease," *Annu Rev Nutr* (1992) 12:279–298.

Kravchenko et al., "Construction of Tandem Artificial Genes Encoding Human Leukocyte Interferon and their Expression as a Part of Polycistronic Template with Coupled Translation," *Bioorganichekaia Khimiia* (1987) 13(9):1186–1193.

Kreis et al., "Biological Effects of Enzymatic Deprivation of L–Methionine in Cell Culture and Experimental Tumor," *Cancer Res* (1973) 33:1866–1869.

Kreis et al., "Effect of Nutritional and Enzymatic Methionine Deprivation upon Human Normal and Malignant Cells in Tissue Culture," *Cancer Res* (1980) 40:634–641.

Kreis et al., "Isolation and Purification of L–Methionine–α–Deamino–γ–Mercaptomethane–Lyase (L–Methioninase) from *Clostridium sporogenes*," *Cancer Res* (1973) 33:1862–1865.

Lapela et al., "Imaging of Uterine Carcinoma by Carbon–11–Methionine and PET," *J Nucl Med* (1994) 35:1618–23.

Leighton, "A Sponge Matrix Method for Tissue Culture" *J Natl Cancer Inst* (1951) 12:545–561.

Leskinen–Kallio et al., "Carcon–11–Methionine and PET is an Effective Method to Image Head and Neck Cancer," *J Nucl Med* (1992) 33:691–695.

Leskinen–Kallio et al., "Uptake of Carbon–11–Methionine and Fluorodeoxyglucose in Non–Hodgkins's Lymphoma: A PET Study," *J Nucl Med* (1991) 32:1211–1218.

Lindholm et al., "Comparison of Fluorine–18–Fluorodeoxyglucose and Carbon–11–Methionine in Head and Neck Cancer," *J Nucl Med* (1993) 34:1711–1716.

Lishko et al., "Depletion of Serum Methionine by Methioninase in Mice," *Anticancer Research* (1993) 13:1465–1468.

Lowry et al., "Protein Measurement with the Folin Phenol Reagent," *J Biol Chem* (1951) 193:265.

Matsumae et al., "Specific Removal of Endotoxin from Protein Solutions by Immobilized Histidine," *Biotechnol Appl Biochem* (1990) 19(1):129–140.

Matteucci et al., "Synthesis of Deoxyoligonucleotides on a Polymer Support," *J Am Chem Soc* (1981) 103:3185–3191.

McCully, "Vascular Pathology of Homocytseinemia: Implications for the Pathogenesis of Arteriosclerosis," *Am J Pathology* (1969) 56:111–128.

McKie et al., "The Primitive Protozoon *Trichomonas vaginalis* Contains Two Methionine γ–Lyase Genes That Encode Members of the γ–Family of Pyridoxal 5'–Phosphate Dependent Enzymes," *J Biol Chem* (1988) 273:5549–5556.

Mecham et al., "The Metabolic Defect of Methionine Dependence Occurs Frequently in Human Tumor Cell Lines," *Biochem Biophys Res Comm* (1983) 117:429–434.

Mineura et al., "Innovative Approach in the Diagnosis of Gliomatosis Cerebri Using Carbon–11–L–Methionine Positron Emission Tomography," *J Nucl Med* (1991) 32:726–728.

Miyazawa et al., "PET Imaging of Non–Small–Cell Lung Carcinoma with Carbon–11–Methionine: Relationship Between Radioactivity Uptake and Flow–Cytometric Parameters," *J Nucl Med* (1991) 34:1886–1891.

Nakayama et al., "Purification and Properties of L–Methionine Gamma–Lyase From Aeromonas SP," *Agric Biol Chem* (1984) 48:2367–2369.

Nieto et al., "Cloning Vectors, Derived from a Naturally Occuring Plasmid of Pseudomonas savastanoi, Specifically Tailored for Genetic Manipulations in Pseudomonas," *Gene* (1990) 87:145–149.

Sambrook et al., Molecular Cloning: A Laboratory Manual, Cold Spring Harbor Press (1989) pp. A.1–A.4.

Sambrook et al., Molecular Cloning: A Laboratory Manual, Cold Spring Harbor Press (1989) pp. 129–1.30.

Sambrook et al., Molecular Cloning: A Laboratory Manual, Cold Spring Harbor Press (1989) pp. 1.74–1.84.

Sambrook et al., Molecular Cloning: A Laboratory Manual, Cold Spring Harbor Press (1989) pp. 18.47–18.59.

Selhub et al., "Association Between Plasma Homocysteine Concentrations and Extracranial Carotid–Artery Stenosis," *New Engl J Med* (1995) 32:286–91.

Shields et al., "Contribution of Labeled Carbon Dioxide to PET Imaging of Carbon–11–labeled Compounds," *J Nucl Med* (1992) 33:581–584.

Soda, "Microdetermination of D–Amino Acids and D–Amino Acid Oxidase Activity with 3–Methyl–2–Benzothiazolone Hydrazone Hydrochloride," *Analytical Biochemistry* (1968) 25:228–235.

Southern, "Detection of Specific Sequences Among DNA Fragments Separated by Gel Electrophoresis," *J Mol Biol* (1975) 98:503–517.

Southern et al., "Transformation of Mammalian Cells to Antibiotic Resistance with a Bacterial Gene Under Control of the SV40 Early Region Promoter," *J Mol Anyl Genet* (1982) 1:327–341.

Stampfer et al., "Can Lowering Homocysteine Levels Reduce Cardiovascular Risk?," *New Engl J Med* (1995) 332:326–329.

Stampfer et al., "A Prospective Study of Plasma Homocyst(e)ine and Risk of Myocardial Infarction in US Physicians," *JAMA* (1992) 268:877–881.

Stern et al., "Enhanced In Vitro Selective Toxicity of Chemotherapeutic Agents for Human Cancer Cells Based on a Metabolic Defect," *J Natl Cancer Inst* (1986) 76:629–639.

Tan et al., "Overexpression and Large–Scale Production of Recombinant 1–Methionine–Alpha–Deamino–Gamma–Mercaptomethane–Lyase for Novel Anticancer Therapy," Protein Expression and Purification (1997) 9(2):233–245.

Tanaka et al., "Purification and Properties of Methioninase from *Pseudomonas Ovalis*," *FEBS Letters* (1976) 66:307–311.

Tarcha, Polymers for Controlled Drug Delivery (CRC Press Boca Raton 1990) pp. 265–273.

Tisdale et al., "Differential Sensitivity of Normal and Leukemic Hemopoietic Cells to Methioninase," *Leuk Res* (1983) 7(2):269–277.

Ueland et al., "Plasma Homocysteine and Cardiovascular Disease," *Atherosclerotic Cardiovascular Disease, Hemostasis, and Endothelial Function* (Marcel Dekler, New York 1992) pp. 183–236.

Vescio et al., "In Vivo–Like Responses of Human Tumors Growing in Three–Dimensional Gel–Supported Primary Culture," *Proc Natl Acad Sci USA* (1987) 84:5029–5033.

Wigler et al., "DNA–Mediated Transfer of the Adenine Phosphoribosyltransferase Locus into Mammalian Cell," *Proc Natl Acad Sci USA* (1979) 76:1373–1376.

Young et al., "Efficient Isolation of Genes by Using Antibody Probes," *Proc Natl Acad Sci USA* (1983) 80:1194–1198.

Zar, Biostatistical Analysis, Prentice Hall, New Jersey (1984) pp. 229–297.

Esaki, N, et al. (1987) *Methods in Enzymology* 143:459–465.

```
           10         20         30         40         50         60
            *          *          *          *          *          *
      GCCGGTCTGT GGAATAAGCT TATAACAAAC CACAAGAGGC GGTTGCCATG CACGGCTCCA
      CGGCCAGACA CCTTATTCGA ATATTGTTTG GTGTTCTCCG CCAACGGTAC GTGCCGAGGT
                                                         Met HisGlySer 70         80         90        100        110        120
            *          *          *          *          *          *
      ACAAGCTCCC AGGATTTGCC ACCCGCGCCA TTCACCATGG CTACGACCCC CAGGACCACG
      TGTTCGAGGG TCCTAAACGG TGGGCGCGGT AAGTGGTACC GATGCTGGGG GTCCTGGTGC
      AsnLysLeuPro GlyPheAla ThrArgAla IleHisHisGly TyrAspPro GlnAspHis 130        140        150        160        170        180
            *          *          *          *          *          *
      GCGGCGCACT GGTGCCACCG GTCTACCAGA CCGCGACGTT CACCTTCCCC ACCGTGGAAT
      CGCCGCGTGA CCACGGTGGC CAGATGGTCT GGCGCTGCAA GTGGAAGGGG TGGCACCTTA
      GlyGlyAlaLeu ValProPro ValTyrGln ThrAlaThrPhe ThrPhePro ThrValGlu 190        200        210        220        230        240
            *          *          *          *          *          *
      ACGGCGCTGC GTGCTTTGCC GGCGAGCAGG CCGGCCATTT CTACAGCCGC ATCTCCAACC
      TGCCGCGACG CACGAAACGG CCGCTCGTCC GGCCGGTAAA GATGTCGGCG TAGAGGTTGG
      TyrGlyAlaAla CysPheAla GlyGluGln AlaGlyHisPhe TyrSerArg IleSerAsn 250        260        270        280        290        300
            *          *          *          *          *          *
      CCACCCTCAA CCTGCTGGAA GCACGCATGG CCTCGCTGGA AGGCGGCGAG GCCGGGCTGG
      GGTGGGAGTT GGACGACCTT CGTGCGTACC GGAGCGACCT TCCGCCGCTC CGGCCCGACC
      ProThrLeuAsn LeuLeuGlu AlaArgMet AlaSerLeuGlu GlyGlyGlu AlaGlyLeu 310        320        330        340        350        360
            *          *          *          *          *          *
      CGCTGGCCTC GGGCATGGGG GCGATCACGT CCACGCTATG GACACTGCTG CGCCCCGGTG
      GCGACCGGAG CCCGTACCCC CGCTAGTGCA GGTGCGATAC CTGTGACGAC GCGGGGCCAC
      AlaLeuAlaSer GlyMetGly AlaIleThr SerThrLeuTrp ThrLeuLeu ArgProGly
```

*FIG. 1A*

```
                370        380        390        400        410        420
                 *  *       *  *       *  *       *  *       *  *       *  *
            ACGAGGTGCT GCTGGGCAAC ACCCTGTACG GCTGCACCTT TGCCTTCCTG CACCACGGCA
            TGCTCCACGA CGACCCGTTG TGGGACATGC CGACGTGGAA ACGGAAGGAC GTGGTGCCGT
            AspGluValLeu LeuGlyAsn ThrLeuTyr GlyCysThrPhe AlaPheLeu HisHisGly 430        440        450        460        470        480
                 *  *       *  *       *  *       *  *       *  *       *  *
            TCGGCGAGTT CGGGGTCAAG CTGCGCCATG TGGACATGGC CGACCTGCAG GCACTGGAGG
            AGCCGCTCAA GCCCCAGTTC GACGCGGTAC ACCTGTACCG GCTGGACGTC CGTGACCTCC
            IleGlyGluPhe GlyValLys LeuArgHis ValAspMetAla AspLeuGln AlaLeuGlu 490        500        510        520        530        540
                 *  *       *  *       *  *       *  *       *  *       *  *
            CGGCCATGAC GCCGGCCACC CGGGTGATCT ATTTCGAGTC GCCGGCCAAC CCCAACATGC
            GCCGGTACTG CGGCCGGTGG GCCCACTAGA TAAAGCTCAG CGGCCGGTTG GGGTTGTACG
            AlaAlaMetThr ProAlaThr TrpValIle TyrPheGluSer ProAlaAsn ProAsnMet 550        560        570        580        590        600
                 *  *       *  *       *  *       *  *       *  *       *  *
            ACATGGCCGA TATCGCCGGC GTGGCGAAGA TTGCACGCAA GCACGGCGCG ACCGTGGTGG
            TGTACCGGCT ATAGCGGCCG CACCGCTTCT AACGTGCGTT CGTGCCGCGC TGGCACCACC
            HisMetAlaAsp IleAlaGly ValAlaLys IleAlaArgLys HisGlyAla ThrValVal 610        620        630        640        650        660
                 *  *       *  *       *  *       *  *       *  *       *  *
            TCGACAACAC CTACTGCACG CCGTACCTGC AACGGCCACT GGAGCTGGGC GCCGACCTGG
            AGCTGTTGTG GATGACGTGC GGCATGGACG TTGCCGGTGA CCTCGACCCG CGGCTGGACC
            ValAspAsnThr TyrCysThr ProTyrLeu GlnTrpProLeu GluLeuGly AlaAspLeu 670        680        690        700        710        720
                 *  *       *  *       *  *       *  *       *  *       *  *
            TGGTGCATTC GGCCACCAAG TACCTGAGCG CCATGGCGA CATCACTGCT GGCATTGTGG
            ACCACGTAAG CCGGTGGTTC ATGGACTCGC CGGTACCGCT GTAGTGACGA CCGTAACACC
            ValValHisSer AlaThrLys TyrLeuSer GlyHisGlyAsp IleThrAla GlyIleVal
```

FIG.1B

```
              730        740        750        760        770        780
               *    *    *    *    *    *    *    *    *    *    *    *
          TGGGCAGCCA GGCACTGGTG GACCGTATAC GTCTGCAGGG CCTCAAGGAC ATGACCGGTG
          ACCCGTCGGT CCGTGACCAC CTGGCATATG CAGACGTCCC GGAGTTCCTG TACTGGCCAC
          ValGlySerGln AlaLeuVal AspArgIle ArgLeuGlnGly LeuLysAsp MetThrGly 790        800        810        820        830        840
               *    *    *    *    *    *    *    *    *    *    *    *
          CGGTGCTCTC GCCCCATGAC GCCGCACTGT TGATGCGCGG CATCAAGACC CTCAACCTGC
          GCCACGAGAG CGGGGTACTG CGGCGTGACA ACTACGCGCC GTAGTTCTGG GAGTTGGACG
          AlaValLeuSer ProHisAsp AlaAlaLeu LeuMetArgGly IleLysThr LeuAsnLeu 850        860        870        880        890        900
               *    *    *    *    *    *    *    *    *    *    *    *
          GCATGGACCG CCACTGCGCC AACGCTCAGG TGCTGGCCGA GTTCCTCGCC CGGCAGCCGC
          CGTACCTGGC GGTGACGCGG TTGCGAGTCC ACGACCGGCT CAAGGAGCGG GCCGTCGGCG
          ArgMetAspArg HisCysAla AsnAlaGln ValLeuAlaGlu PheLeuAla TrpGlnPro 910        920        930        940        950        960
               *    *    *    *    *    *    *    *    *    *    *    *
          AGGTGGAGCT GATCCATTAC CCGGGCCTGG CGAGCTTCCC GCAGTACACC CTGGCCCGCC
          TCCACCTCGA CTAGGTAATG GGCCCGGACC GCTCGAAGGG CGTCATGTGG GACCGGGCGG
          GlnValGluLeu IleHisTyr ProGlyLeu AlaSerPhePro GlnTyrThr LeuAlaArg 970        980        990       1000       1010       1020
               *    *    *    *    *    *    *    *    *    *    *    *
          AGCAGATGAG CCAGCCGGGC GGCATGATCG CCTTCGAACT CAAGGGCGGC ATCGGTGCCG
          TCGTCTACTC GGTCGGCCCG CCGTACTAGC GGAAGCTTGA GTTCCCGCCG TAGCCACGGC
          GlnGlnMetSer GlnProGly GlyMetIle AlaPheGluLeu LysGlyGly IleGlyAla 1030       1040       1050       1060       1070       1080
               *    *    *    *    *    *    *    *    *    *    *    *
          GGCGGCGGTT CATGAACGCC CTGCAACTGT TCAGCCGCGC GGTGAGCCTG GGCGATGCCG
          CCGCCGCCAA GTACTTGCGG GACGTTGACA AGTCGGCGCG CCACTCGGAC CCGCTACGGC
          GlyTrpTrpPhe MetAsnAla LeuGlnLeu PheSerArgAla ValSerLeu GlyAspAla
```

*FIG. 1C*

```
        1090       1100       1110       1120       1130       1140
          *    *     *    *     *    *     *    *     *    *     *    *
       AGTCGCTGGC GCAGCACCCG GCAAGCATGA CTCATTCCAG CTATACCCCA GAGGAGCGTG
       TCAGCGACCG CGTCGTGGGC CGTTCGTACT GAGTAAGGTC GATATGGGGT CTCCTCGCAC
       GluSerLeuAla GlnHisPro AlaSerMet ThrHisSerSer TyrThrPro GluGluArg 1150       1160       1170       1180       1190       1200
          *    *     *    *     *    *     *    *     *    *     *    *
       CGCATTACGG CATCTCCGAG GGGCTGGTGC GGTTGTCGGT GGGGCTGGAA GACATCGACG
       GCGTAATGCC GTAGAGGCTC CCCGACCACG CCAACAGCCA CCCCGACCTT CTGTAGCTGC
       AlaHisTyrGly IleSerGlu GlyLeuVal TrpLeuSerVal GlyLeuGlu AspIleAsp 1210       1220       1230       1240       1250       1260
          *    *     *    *     *    *     *    *     *    *     *    *
       ACCTGCTGGC CGATGTGCAA CAGGCACTCA AGGCGAGTGC CTGAACCCGT CACGGATGAG
       TGGACGACCG GCTACACGTT GTCCGTGAGT TCCGCTCACG GACTTGGGCA GTGCCTACTC
       AspLeuLeuAla AspValGln GlnAlaLeu LysAlaSerAla 1270       1280       1290       1300       1310       1320
          *    *     *    *     *    *     *    *     *    *     *    *
       GTCAATGCAA TGGTGGCAAT GATGAACCTT GTGCCTGGCG ACGGCGTGCC CGGTGACAGC
       CAGTTACGTT ACCACCGTTA CTACTTGGAA CACGGACCGC TGCCGCACGG GCCACTGTCG 1330       1340       1350       1360
          *    *     *    *     *    *     *    *     *
       GACCCTGGCG AAACTGCAGA GTGGCTGGAG CGCTGGAGT CGACCCTGG
       CTGGGACCGC TTTGACGTCT CACCGACCTC CGCGACCTCA GCTGGGACC
```

HIGH EXPRESSION MODULES CONTAINING TWO OR MORE TANDEM COPIES OF A METHIONINASE ENCODING SEQUENCE

RELATED APPLICATIONS

This application is a continuation of U.S. Ser. No. 08/908,860, filed Aug. 8, 1997, which is a continuation-in-part of U.S. Ser. No. 08/642,541, filed May 3, 1996 and now U.S. Pat. No. 5,891,704, which is a continuation in part of U.S. Ser. No. 08/486,519, filed Jun. 5, 1995 and now U.S. Pat. No. 5,715,835, which is a continuation in part of U.S. Ser. No. 08/424,300, filed Apr. 24, 1995 and now U.S. Pat. No. 5,690,929, which application was filed under section 371 based on PCT U.S. 93/11311 filed Nov. 19, 1993 and which is a continuation in-part of Ser. No. 07/979,165 filed Nov. 19, 1992 now abandoned. The contents of these applications are incorporated herein by reference.

TECHNICAL FIELD

The present invention relates to methioninase expression systems containing two or more tandem nucleotide sequences that encode methioninase and to methods to produce recombinant methioninase from them. This system of production results in high amounts of methioninase activity. The methioninase thus produced is useful in anti-methionine and antihomocysteine therapy.

BACKGROUND

Therapeutic drug-based treatment of cancer is directed at the use of medicinals which selectively inhibit or kill the cancer cells while not harming normal tissue function beyond acceptable amounts. The difficulty with conventional chemotherapy has been the toxicity of therapeutic drugs for normal tissue.

Many tumors have been shown to have absolute requirement for methionine in a variety of cell types and evaluated tumor tissues, including tumors of the colon, breast prostate, ovary, kidney, larynx melanoma, sarcoma, lung, brain, stomach and bladder as well as leukemias and lymphomas. Methionine dependence has been defined as an inability of tumors to grow when methionine is replaced by homocysteine in the growth medium. See, for example, Chello et al., *Cancer Res*, 33:1898–1904, 1973; and Hoffman, *Anticancer Res*, 5:1–30, 1985.

Methionine depletion has been shown to synchronize selectively methionine-dependent tumor cells into late $S/G_2$ phase of the cell cycle. Hoffman et al, *Proc Natl Acad Sci USA*, 77:7306–7310, 1980. Using antimethionine chemotherapy which is methionine deprivation, followed by depletion of methionine and coupled with exposure to an antimitotic agent, tumor cells have been selectively eliminated from cocultures of normal and tumor cells, resulting in cultures of normal cells proliferating vigorously. Stem et al., *J Natl Cancer Inst*, 76:629–639, 1986.

In order for methionine-dependent chemotherapy to be conducted in vivo, it is necessary to have a means to effectively deplete serum of circulating methionine. Methionine depletion methods have not been described that reduce circulating methionine levels in vivo in a manner sufficient to be effective in antitumor therapies.

Methioninase, an enzyme which degrades methionine, has been purified from a variety of bacterial sources, and has been reported to slow the rate of tumor cell proliferation in vitro. Kreis et al., *Cancer Res*, 33:1862–1865, and 1866–1869, 1973; Tanaka et al., *FEBS Letters*, 66:307–311 1976; Ito et al., *J Biochem* 79:1263–1272, 1976; and Nakayama et al., *Agric Biol Chem* 48:2367–2369, 1984.

Kreis et al., *Cancer Res* 33:1866–1869, 1973, have described the use of highly impure methioninase preparations isolated from *Clostridium sporogenes* at 1150 units/kg/day to inhibit growth of carcinosarcoma cells implanted in a mouse model. Although the enzyme apparently reduced primary tumor cell growth, it was not reported to reduce the T/C (treated versus control) ratio of tumor diameter below 50%, and was not reported to have any effect on metastasis. The authors also indicated that tumor specificity of the methioninase cannot be expected without other unspecified interventions, and further do not comment on the possibility that endotoxin, or other components of the impure preparation, were responsible for the effects observed. The only toxicity studies reported were absence of animal body weight loss after the duration of the treatment, and negative gross examination for toxicity. Further, the authors report that the enzyme had a serum half life of 4 hours. Kreis et al., *Cancer Res* 33:1866–1869, 1973, further reported the use of a methionine-free diet as a means to deplete methionine as an antitumor therapy, but the diet did not slow tumor growth as effectively as the use even of an impure preparation of methioninase and resulted in the undesirable side effect of continuous loss of weight of the animal.

The parent applications herein disclose effective chemotherapy of tumors directed at reducing the amount of methionine as to provide a beneficial antitumor effect without deleterious injury using methioninase. The present invention improves the disclosed therapeutic and diagnostic methods and composition by providing a method to produce commercially viable quantities of highly pure recombinant methioninase, using expression systems containing at least two copies of the methioninase gene.

DISCLOSURE OF THE INVENTION

The present invention is based, in part, on the generation of methioninase expression systems containing two or more tandem copies of methioninase encoding nucleotide sequences. The expression systems of the present invention can produce recombinant methioninase in an appropriate host cell, such as *E. coli*, at levels ranging from about 40–75% of total cellular protein.

In a preferred embodiment methioninase expression systems containing two or more tandem copies of the *P. putida* methioninase gene operably linked to a T7 RNA polymerase promoter are described. These systems have been used to produce recombinant methioninase at about 1 to 4 gram/liter, with an activity of about 6.4 to about 12.4 units/mL and a specific activity of about 3.8 to about 10.2 units/mg before purification, using appropriate incubation conditions and purification methods.

The invention further provides methods of producing recombinant methioninase using cells containing the methioninase expression system of the present invention.

Substantially pure recombinant methioninase produced using cells containing the methioninase expression systems of the present invention is useful in compositions for diagnostic and therapeutic use, particularly in methods for inhibiting tumor cell growth to lower homocysteine levels in patients to reduce the risk of, and to treat, cardiovascular diseases, obesity and negative symptomologies of aging, as well as to deplete methionine for tumor diagnosis and imaging.

The recombinant methioninase may be provided in chemically modified forms, for example by coupling to polymers such as polyethylene glycol (PEG).

BRIEF DESCRIPTION OF THE DRAWINGS

The drawings are not necessarily to scale, and certain features of the invention may be exaggerated in scale and shown in schematic form in the interest of clarity and conciseness.

MODES OF CARRYING OUT THE INVENTION

As used herein, a "multicopy" or "multiple" expression system refers to a nucleic acid molecule that contains one or more expression control elements that direct the transcription and translation of two or more tandem copies of a nucleotide sequence that encodes methioninase. Preferably, the expression system will contain from two to four tandem copies of the methioninase encoding sequences which may be the same or different. If desired, the nucleotide sequences can be modified from those found in nature to contain silent mutations to provide codons preferred by E. coli. Such codons are known in the art—see, e.g., U.S. Pat. Nos. 4,356,270 and 4,571,421 to Genentech.

The resulting recombinant methioninase produced represents from about 40–75% of total cellular protein, preferably more than 50% of total cellular protein. The preferred expression control element is the T7 RNA polymerase promoter. Other examples of RNA polymerase promoters include, but are not limited to, the Tac and Trc promoters.

Figure 3:
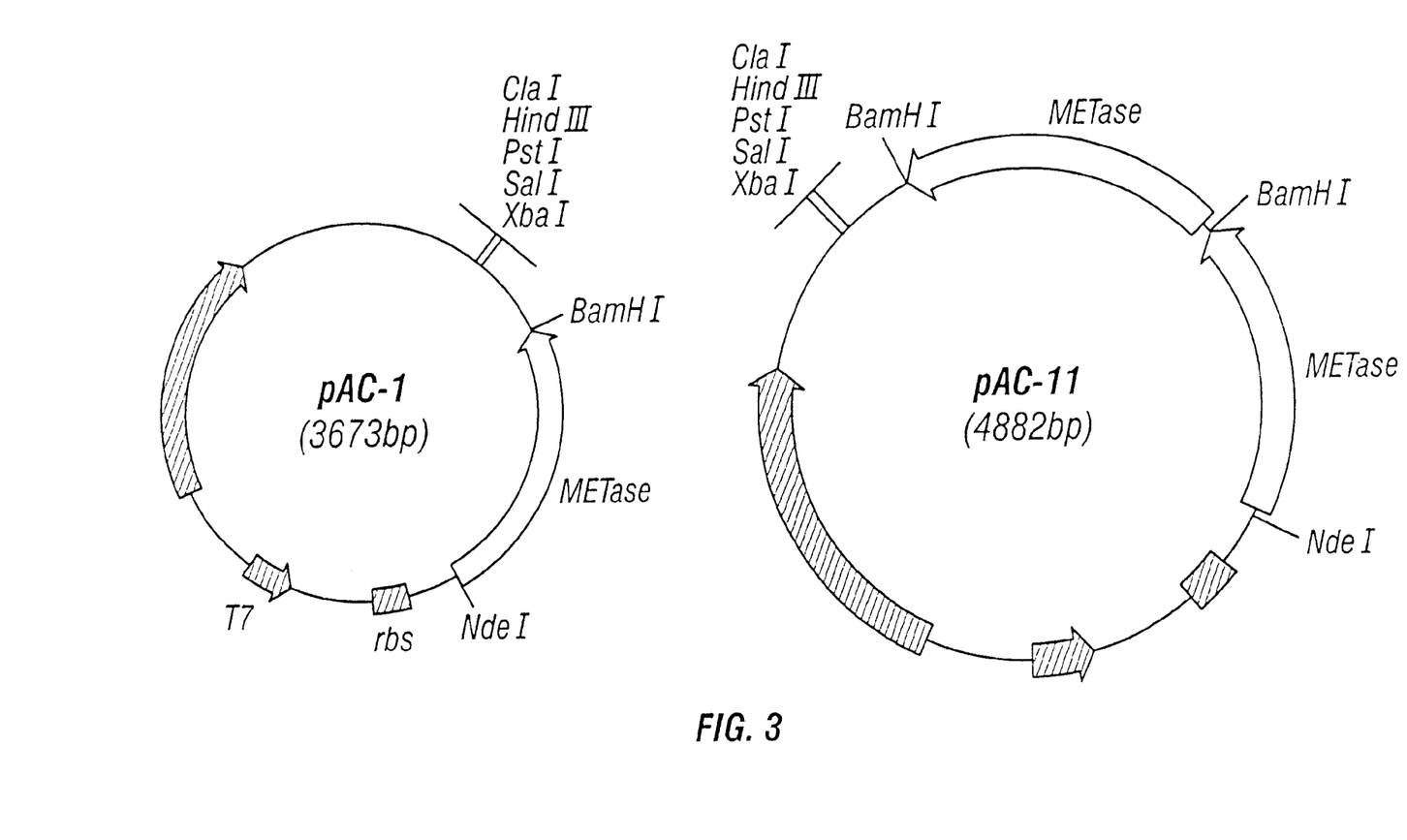
FIG. 3 is a diagram of a one-copy and a two-copy methioninase expression system.

As used herein, a nucleotide sequence is said to "encode" methioninase when the transcription and translation of the sequence results in the production of a protein having methioninase activity. Copies of methioninase encoding nucleotide sequences are "tandemly" omited when they are provided as direct repeats of the same or different methioninase-encoding sequence. FIG. 3 provides a diagram of a multiple expression system that contains two tandem copies of the P. putida methioninase gene.

L-Methioninase (L-methionine-α-deamino-γ-mercaptomethane-lyase or methioninase) is an enzyme that degrades methionine by deamination and dethiomethylation, to produce α-ketobutyrate. One method to measure methioninase activity is to determine the amount of α-ketobutyrate formed. One unit (U) of methioninase is defined as an amount of enzyme that produces 1 micromole of α-ketobutyrate per minute from methionine under the standard assay conditions described by Ito et al., *J Biochem*, 79:1263–1272, 1976; and Soda, *Analyt Biochem* 25:228–235, 1968.

The methioninase-encoding nucleotide sequence may be unaltered as, obtained from an organism that naturally produces this enzyme or may be modified to result in one or more amino acid substitutions, deletions or additions.

Figure 1A:
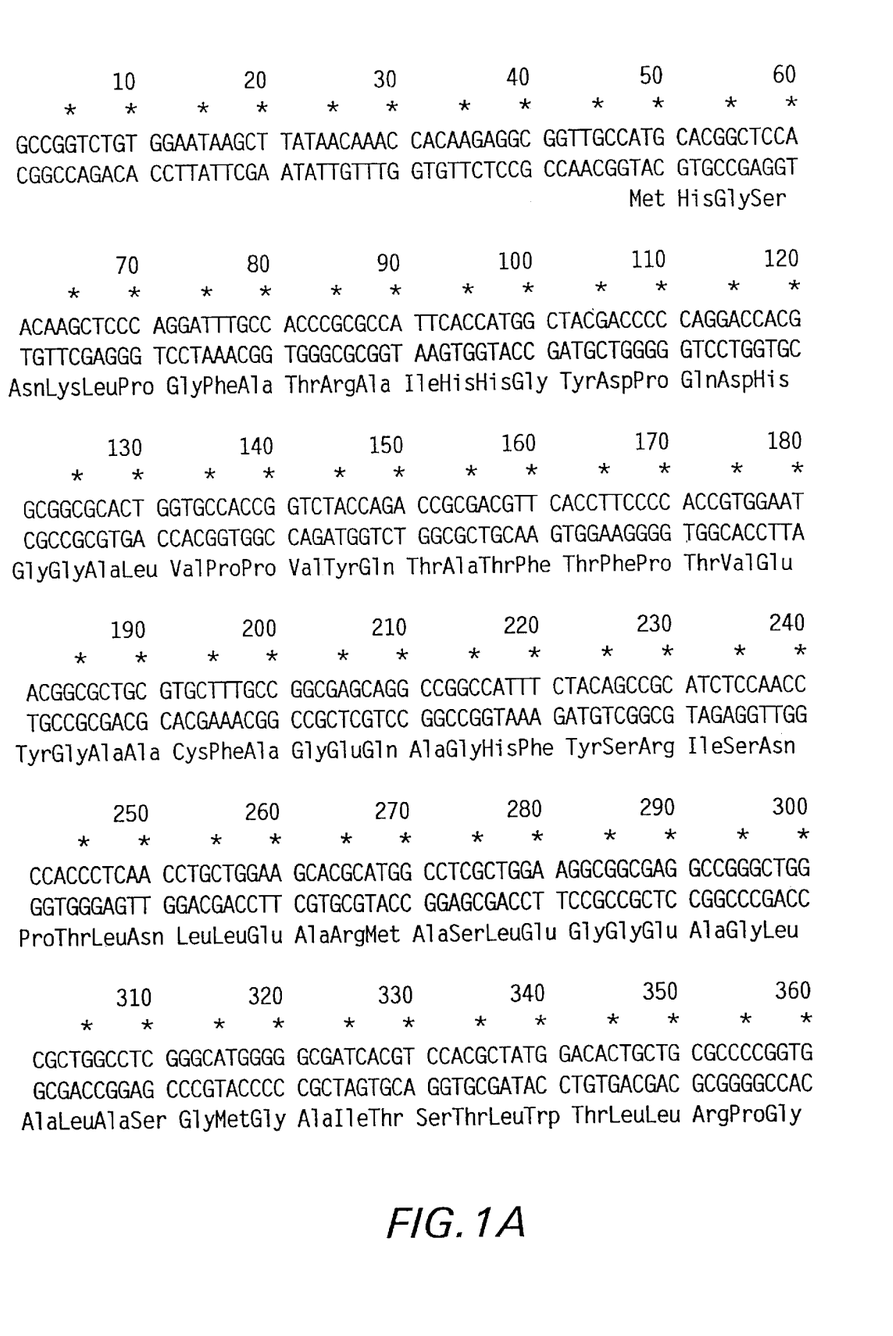
FIGS. 1A and 1B provide the nucleotide (and corresponding amino acid sequence) of a methioninase encoding DNA molecule isolated from P. putida.
Figure 1B:
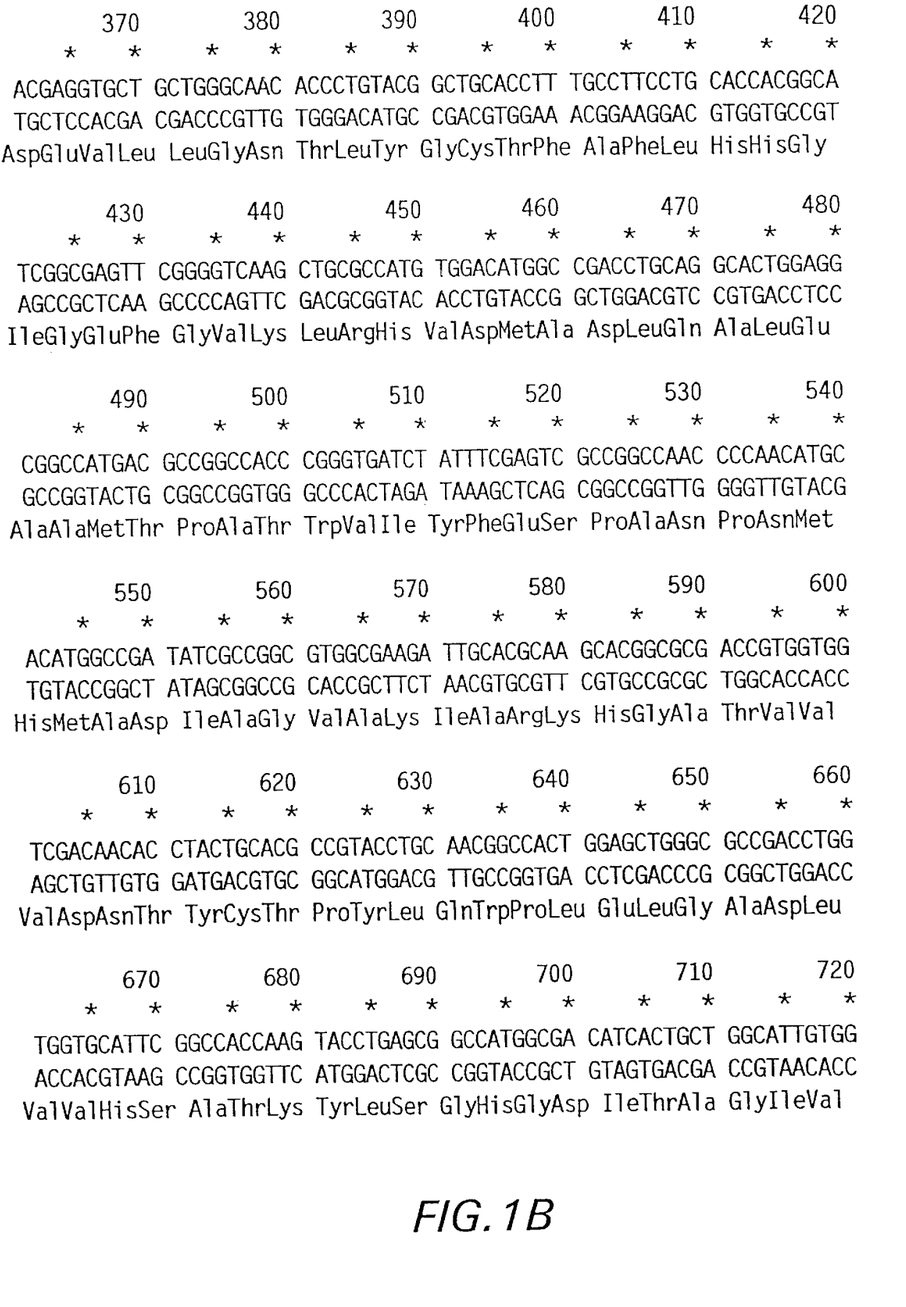
Figure 1C:
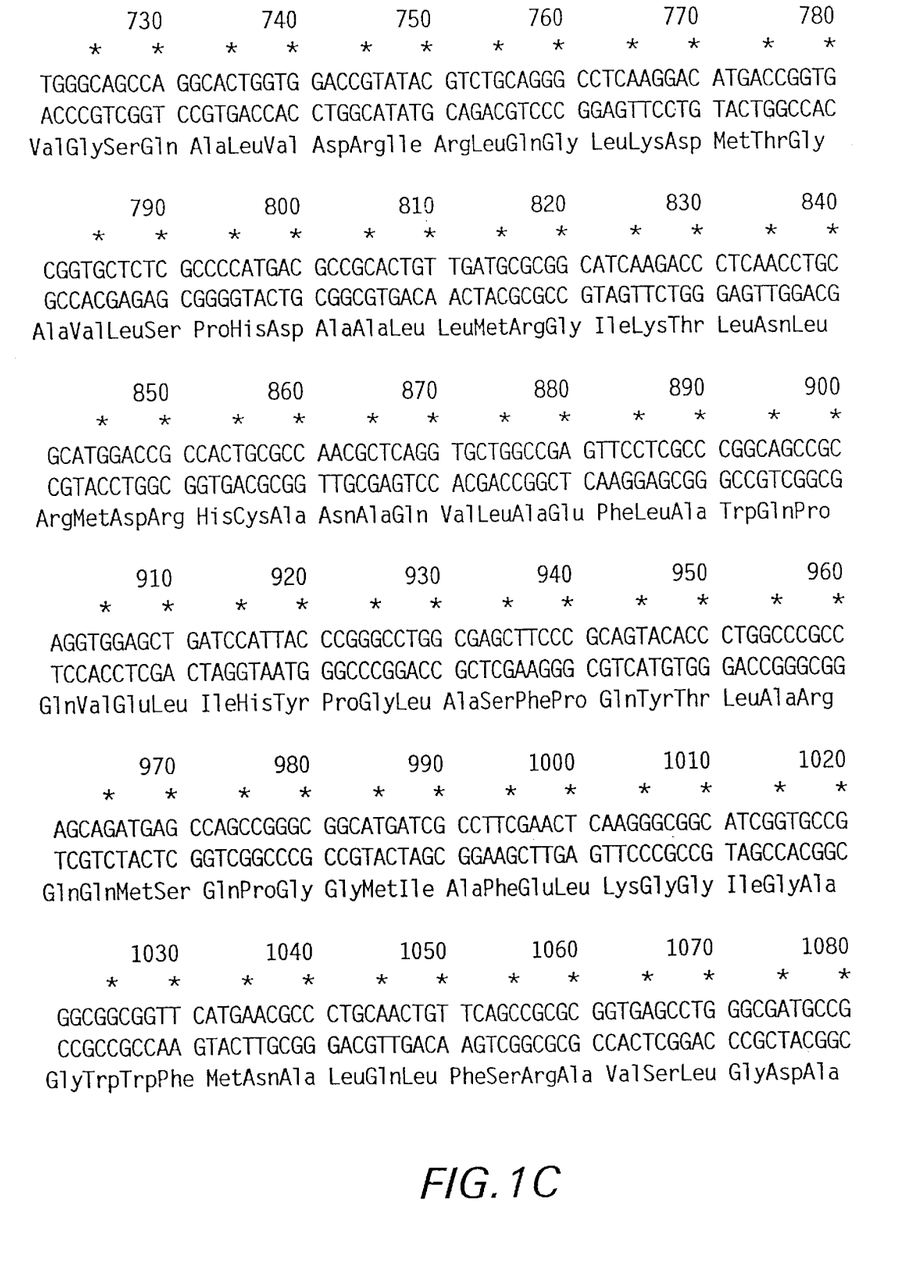
Figure 1D:
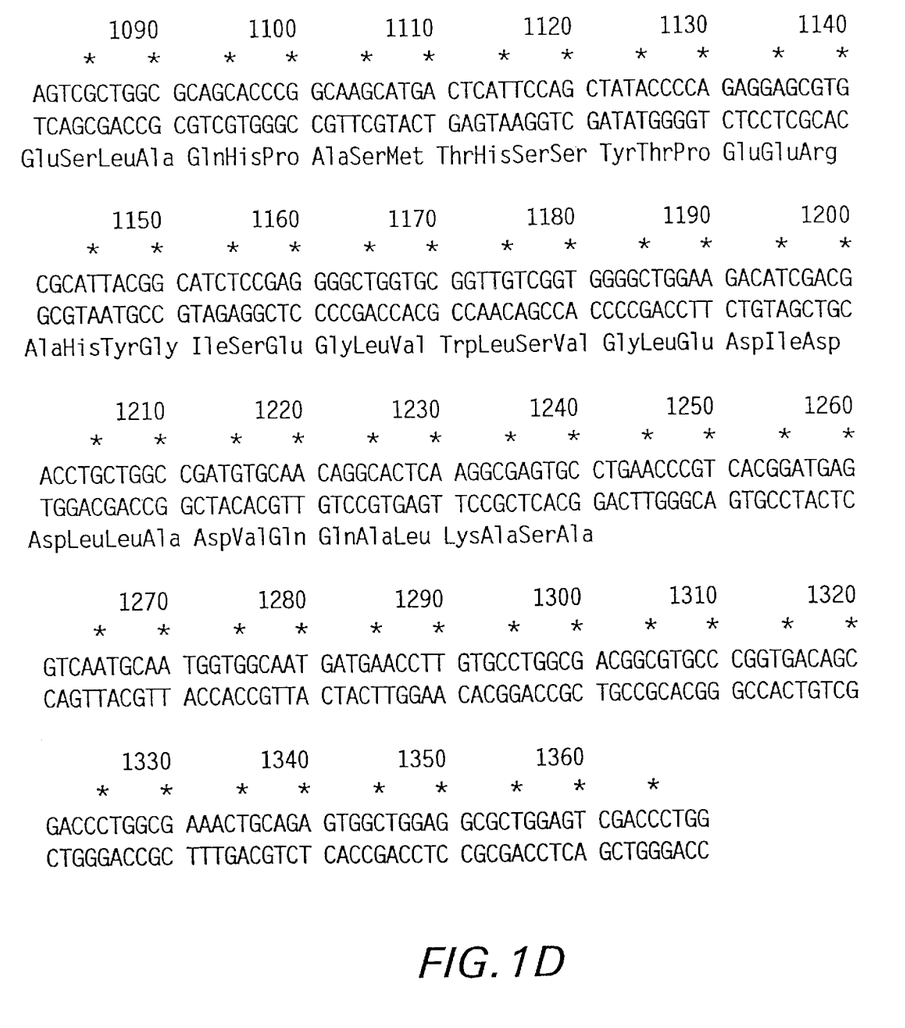

The methioninase-encoding nucleic acid molecule, whether altered or unaltered, can be derived from any organism that naturally produces methioninase. The preferred source of the methioninase-encoding nucleic acid molecule is *Pseudomonas putida*. Example 1 discloses the isolation and sequencing of a methioninase-encoding nucleic acid molecule from *P. putida* (See FIG. 1). Other preferred sources include, but are not limited to, *Trichomonas vaginalis, Nippostrongylus brasiliensis*, and *Fusobacterium Sp*.

The multicopy expression systems can be prepared using art known methods, such as restriction digestion followed by ligation.

If desired, the methioninase encoding sequences may be altered so as to facilitate purification of the resulting protein, for example, by adding a polyhistidine stretch at either the amino or carboxy terminus. $Ni^{++}$ sepharose can then be used to purify the resulting fusion protein.

The present invention further provides vectors containing one or more of the multicopy expression systems of the present invention. Vectors are DNA molecules that can be introduced into host cells and may be capable of autonomous replication within a host. Vectors may thus contain an episomal origin of replication derived from a naturally occurring plasmid, a genomic origin of replication, or may be derived from a viral genome. The choice of the vector to which an expression system of the present invention is inserted depends on the functional properties desired, e.g., presence of a suitable marker, and the host cell to be modified.

In one preferred embodiment, the vector includes a procaryotic replicon, such as the ColEl replicon, as well as a selectable marker such as a drug resistance.

Eucaryotic expression vectors can also be used, are well known in the art and are available from several commercial sources. Typical such vectors are pSVL and pKSV-10 (Pharmacia), pBPV-1/pML2d (International Biotechnologies, Inc.), pTDT1 (ATCC, #31255), and the vector pCDM8 described herein. High level expression vectors can further be generated using insect cell expression systems such as a bacculovirus based vector system.

The host cells for methioninase production can be either procaryotic or eucaryotic. A preferred procaryotic host is *E. coli*. In the Examples that follow, the DH5α and BL21(DE3) strains of *E. coli* were used.

Preferred eucaryotic host cells include insect cells, yeast cells and mammalian cells, preferably insect cells such as SP6 and vertebrate cells such as those from a mouse, rat, monkey or human fibroblastic cell line. Other preferred eucaryotic host cells include Chinese hamster ovary (CHO) cells available from the ATCC as CCL61, NIH Swiss mouse embryo cells NIH3T3 available from the ATCC as CRL 1658, baby hamster kidney cells (BHK), and the like eucaryotic tissue culture cell lines.

Transformation of an appropriate host with a multicopy methioninase expression system of the present invention is accomplished by well known methods that typically depend on the type of host and vector used. Transformation of procaryotic host cells is preferably by electroporation or salt treatment; for example, see Cohen et al, *Proc Natl Acad Sci USA* 69:2110, 1972; and Maniatis et al., *Molecular Cloning, A Laboratory Mammal*, Cold Spring Harbor Laboratory, Cold Spring Harbor, N.Y. (1982). Transformation of eucaryotic cells is preferably by electroporation or the use of a cationic lipid, for example, see Graham et al., *Virol* 52:456, 1973; and Wigler et al., *Proc Natl Acad Sci USA* 76:1373–76, 1979.

Successfully transformed cells, i.e., cells that contain a multicopy expression system of the present invention, can be identified by well known techniques. Cells from individual colonies can be harvested, lysed and their DNA content examined for the presence of the rDNA using a method such as that described by Southern, *J Mol Biol*, 98:503, 1975, or Berent et al., *Biotech* 3:208, 1985. Attentively, copending application U.S. Ser. No.08/642,541 discloses a rapid screening method to identify transformants which express high levels of recombinant methioninase based on a color cast of colonies formed on solid media.

Recombinant methioninase is produced at commercially significant levels using a host transformed with one or more of the multicopy methioninase expression systems of the present invention. Such a transformed host will express recombinant methioninase at a level from about 40–75% of total cellular protein. The protein may be purified if desired.

Figure 2:
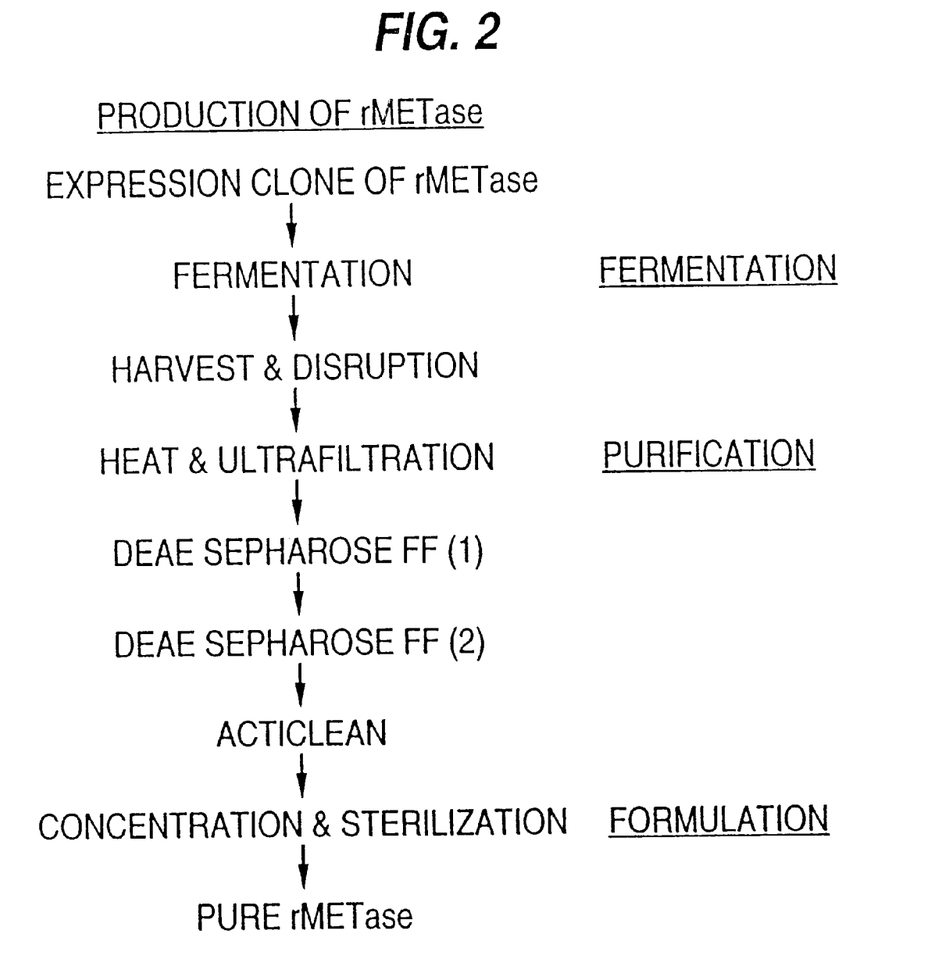
FIG. 2 provides an outline of the purification steps used to obtain highly pure, endotoxin free methioninase.

A preferred method for purification is shown in FIG. 2 and comprises the steps of:

a) heating an extract of a transformed cell that contains methioninase in aqueous buffers from about 40–60° C. for about 1–10 min., preferably 50° C. for 1 min.;

b) centrifuging the heated extract from about 10K to 20K rpm in a GS-3 rotor (Sorvall, Du Pont) for about 15 min. to 1 hour, preferably at about 13K rpm for about 30 min. at 4° C.;

c) ultrafiltering the supernatant using a filter of about 50K to 100K pore size, preferably a Millipore Pre/Scale:TFF PLHK 100 K 2.5 ft$^2$ cartridge using a 10 mM potassium phosphate buffer (pH 8.3);

d) performing DEAE ion exchange chromatography in low ionic strength (from about 10–50 mM) KCl in a 10–20 mM potassium phosphate buffer at about pH 7.0–7.6, and collecting fractions containing methioninase eluted in a 40–200 mM KCl gradient, preferably using DEAE-Sepharose FF column;

e) performing a second DEAE ion exchange chromatography in medium ionic strength (50–100 mM) KCl in a 10–20 mM potassium phosphate buffer at about pH 8.0–8.6, and collecting fractions containing methioninase eluted in a phosphate buffer (pH 8.3) eluted in 100–200 mM KCl, preferably using DEAE-Sepharose FF column; and f) contacting said fractions collected in step (e) with a chromatography medium capable of absorbing endotoxin, and collecting the eluant, thereby removing endotoxin from said eluant to form endotoxin-free methioninase having at least 20 units methioninase activity per milligram protein and from 1–100 ng of endotoxin per mg protein, preferably using an ACTI-CLEAN® ETOX column.

The cell extract is prepared from a host cell that has been altered to contain one of the multicopy methioninase expression systems of the present invention. For bacterial cell extracts, the extracts are generally prepared by first harvesting and washing bacterial cell cultures to form a cell paste/pellet, depending upon whether harvesting is by centrifugation or by hollow fiber filtration, which methods are generally well known.

The cells are then disrupted using conventional means. Preferably the cells are disrupted using a homogenizer, such as a cavitator-type homogenizer, for example, a Microfluidics Corp. Model #HC8000.

The resulting suspension is heated to precipitate selective proteins and other insoluble materials. Typical heating conditions are from about 45–60° C. for 1–10 minutes. Preferred is a heating step of 50° C. for 1 minute.

The heated extract is centrifuged to remove debris, and the supernatant is filtered and applied to DEAE ion-exchange chromatography medium in two steps as described above.

Preferred adsorption and elution conditions are described in the Examples. Any of a variety of DEAE ion exchange column chromatography media can be used in these steps, and the choice of media is not to be construed as limiting. Commercial sources include Pharmacia Fine Chemicals, BioRad, and Sigma.

Thereafter, endotoxin is removed to produce a protein having acceptable levels of endotoxin as recited earlier. The endotoxin removal step can be carried out in any of a variety of well known means, including contacting the protein in solution with a chromatographic medium capable of adsorbing endotoxin, and eluting the endotoxin-free protein. The preferred commercial reagent for use in removing endotoxin is Acticlean® Etox.

Therapeutic Compositions

The substantially isolated recombinant methioninase produced using a host transformed with one of the multicopy methioninase expression systems of the present invention may be formulated into therapeutic compositions.

These compositions will preferably contain recombinant methioninase that has a specific activity of about 10 to 50 units (U) per mg protein, typically about 16 tp 24 U/mg.

For inclusion in such compositions, the methioninase is preferably substantially purified. By substantially purified is meant that the enzyme is at least 90% pure by weight, preferably at least 95% pure, and more preferably at least 99% pure, or essentially homogeneous. Homogeneity can be affirmed by polyacrylamide gel electrophoresis (PAGE or SDS-PAGE), to provide only a single detectable band.

The recombinant methioninase should be substantially free of endotoxins, such as bacterial lipopolysaccharides, due to the undesirable side effects associated with endotoxins when physiologically contacted in a mammal, as by i.v. or i.p. administration. By substantially free is meant less than about 10 nanograms (ng) endotoxin per milligram (mg) recombinant methioninase protein, preferably less than 1 ng/mg and more preferably less than 0.1 ng/mg.

The therapeutic compositions may further comprise a physiologically tolerable carrier. As used herein, the terms "pharmaceutically acceptable", "physiologically tolerable" and grammatical variations, both referring to compositions, carriers, diluents and reagents that the materials are capable of administration to or upon a mammal or human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified. In addition, a therapeutic amount of recombinant methioninase can be present in a ointment or on a diffusible patch, such as a bandage, as to afford local delivery of the agent.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, or the like and combinations thereof In addition, if desired, the composition can contain minor amounts of auxiliary substances such as wetting or emulsifying agents, pH buffering agents and the like which enhance the effectiveness of the active ingredient.

The methioninase may be supplied as a pharmaceutically acceptable salts such as acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water, as described herein. Exemplary of such additional liquid phases are glycerin, vegetable oils such as cottonseed oil, organic esters such as ethyl oleate, and water-oil emulsions, particularly the liposome compositions described earlier.

A therapeutic composition contains an effective amount of recombinant methioninase, typically an amount of at least 0.1 weight percent of active protein per weight of total therapeutic composition, and preferably is at least about 25 weight percent. A weight percent is a ratio by weight of recombinant methioninase protein to total composition. Thus, for example, 0.1 weight percent is 0.1 grams of recombinant methioninase per 100 grams of total composition.

Controlled delivery of the recombinant methioninase can also be effected which further shields the recombinant methioninase protein from degradation and enhances the serum half-life.

Therapeutic compositions may also be delivery vehicles such as polymers, polymeric vehicles, particulates, latexes, coacervates, ion-exchange resins, liposomes, enteric coatings, mediators, bioadhesives, microcapsules, hydrogels, and the like vehicles. Exemplary drug delivery vehicles including liposomes are described at least by Tarcha in "Polymers For Controlled Drug Delivery", CRC Press, Boca Raton, 1990.

The recombinant methioninase may be chemically modified, for example by conjugation to a polymer or by otherwise altering the covalent structure without changing the primary amino acid sequence. Preferable polymers are polyalkylene oxides or polysaccharides. Coupling to a polymer increases the serum half-fife and decreases the immunogenicity or antigenicity of the resulting compound.

A preferred polymer is polyethylene glycol, particularly MSC-5000 PEG, polyethylene oxide, polypropylene oxide, copolymers of ethylene oxide, and copolymers of propylene oxide. Methods for chemically modifying proteins are well known to the art and can readily be used to modify the recombinant methioninase. See, for example, PCT/US93/11311.

Administration and Utility

Methioninase can be used in diagnostic and therapeutic methods that have been developed and described elsewhere. See PCT/US93/11311. For example, methioninase is used 1) as an antitumor agent in a variety of modalities, such as by depleting methionine from tumor cells, 2) to induce cell cycle stasis in tumor cells followed by cell synchronization and the use of antimitotic agents, 3) in combination with antimitotic and cell cycle-specific cytotoxic agents, 4) to deplete cellular methionine prior to labeling with methionine, which can be used in tumor diagnosis and localization, and 5) to deplete serum homocysteine to prevent and cure cardiovascular diseases that are mediated by high serum levels of homocysteine. Recombinant methioninase prepared according to the present invention has now been administered to nine patients wherein infusion dosage of up to 20,000 units, infused over ten hours, had no significant side effects and yielded a depletion of methionine for 10 hours following infusion.

The following examples relating to this invention are illustrative and do not limit the invention.

EXAMPLE 1

Isolation of Nucleic Acid Molecules Encoding Methioninase

Genomic DNA of *Pseudomonas putida* AC-1, derived from ATCC 8209, was used as template; the primers used were as follows:

t1:5'-GCCGGTCTGTGGAATAAGCT-3' (Sense) (SEQ ID NO. 1)
HindIII t2:5'-CCAGGGTCGACTCCAGCGCC-3' (Antisense) (SEQ ID NO. 2)
SalI

```
                                    (SEQ ID NO. 1)
     t1:5'-GCCGGTCTGTGGAATAAGCT-3' (Sense)
                          HindIII (SEQ ID NO. 2)
     t2:5'-CCAGGGTCGACTCCAGCGCC-3' (Antisense)
              Sal I
```

The PCR reaction condition was as follows: first denaturation at 95° C. for 10 minutes, then 5 cycles of denaturation at 94° C. for 30 seconds, annealing at 60° C. for 30 seconds, and extension at 72° C. for 2 minutes; then 25 cycles of denaturation at 94° C. for 30 seconds, 60° C. for 30 seconds, then extension at 72° C. for 1.5 minutes; then final extension at 72° C. for 10 minutes. The PCR amplified products are two bands of which the 1365 bp band was collected, and purified as the insert ONCase-1 DNA.

The ONCase-1 DNA was ligated with pT7Blue T-vector (Novagen) at the EcoR V T-cloning site. The pONCase-1 DNA was transformed into DH5-α bacterial cells using standard procedures.

DNA sequencing was performed using T7 DNA polymerase and the dideoxy nucleotide termination reaction. The primer walking method was used. [35S] dATP was used for labeling. Sequencing reactions were analyzed on 6% polyacrylamide wedge or non-wedge gels containing 8M urea. DNA samples were loaded in the order of ACGT. DNA sequences were analyzed by MacVector. The DNA sequence and corresponding amino acid sequence are provided in FIG. 1.

EXAMPLE 2

High Expression Clones

The pONCase-1 clone was used as a template, the primers used are as follows:

```
t14.5'-GGAATTCCATATGCACGGCTCCAACAAGC-3' (Sense) (SEQ ID NO. 3)
              NdeI t15.5'-AGTCATCCTAGGTCACATCATCATCATCATCATGGCACTCGCCTTGAGTGC-3'
           BamHI                (Antisense) (SEQ ID NO. 4)

t18.5'-AGTCATCCTAGGTCAGGCACTCGCCTTGAGTGC-3'
           BamHI   (Antisense) (SEQ ID NO. 5)
```

The PCR reaction condition was as follows: first denaturation at 95° C. for 10 minutes, then 5 cycles of denaturation at 94° C. for 1 minute, annealing at 56° C. for 1.5 minutes, and extension at 72° C. for 2 minutes; then 20 cycles of denaturation at 94° C. for 30 seconds, 56° C. for 30 seconds, then extension at 72° C. for 1.5 minutes; then final extension at 72° C. for 10 minutes. Two PCR amplified products, ONCase-2 (1238 bp), ONCase-3 (1220 bp) band were collected and purified.

The DNA of ONCase-2 and ONCase-3 DNA was digested with NdeI and BamHI and ligated with the pT7.7 vector at the NdeI and BamHI cloning sites. The pONCase-2 and pONCase-3 DNA sequences were then transformed into BL21 (DE3) bacterial cells using standard procedures.

The positive clones were selected from ampicillin-containing plates. After storage at 4° C. for 24 hours, the positive clones which expressed high level of recombinant methioninase had a distinct pink color that allowed their identification and selection. The methioninase expression levels of the positive clones were determined by activity assay. Two high expression clones were selected as the pAC-1 clone which contained ONCase-3 and as the pAC-2 clone which contained ONCase-2.

The tetracycline resistance gene was obtained from pBR322 at the AvaI and ClaI sites. The AvaI end was filled into a blunt end, ligated with pAC-1 and digested with the BamHI and ClaI, with the BamHI end filled into a blunt end. Positive clones which became pink after storage at 4° C. for 24 hours were selected from tetracycline-containing plates. A high expression recombinant methioninase clone, pAC-3, was chosen by activity assay.

The tetracycline-resistance gene was also obtained from pBR322 at the AvaI and HindIII sites. The AvaI end was filed into a blunt end, and was ligated with pAC-1 which was digested with the HindIII and ClaI, with the ClaI end filled into a blunt end. Positive clones which became pink after storage at 4° C. for 24 hours were selected from tetracycline-containing plates. A high expression recombinant methioninase clone pAC-4 was determined by activity assay. The levels of expression obtained from these vectors are shown in Table 1.

TABLE 1 rMETase Expression Clones

| Clone | Vector | Antibiotic Resistance | Promoter | Fusion | Expression* (g/l) |
|---|---|---|---|---|---|
| pAC-1 | pT7.7 | Amp | T7 | — | 1.0 |
| pAC-2 | pT7.7 | Amp | T7 | His. Tag | 0.5 |
| pAC-3 | pT7.7 | Tc | T7 | — | 0.5 |
| pAC-4 | pT7.7 | Tc | T7 | — | 1.0 |

*Expression level in shaking flask (TB medium, 37° C., 400 rpm, 36 hours).

EXAMPLE 3

Generation of a Tandem Methioninase Expression System

The plasmid pAC-1 was isolated from the amplified cell bank with QIA prep Spin Miniprep Kit (Quiagen), and then digested with BamHI to obtain the host vector containing a single methioninase encoding nucleotide sequence.

ONCase-3 was digested with the NdeI, filled in with Klenow Fill-in Kit (Stratagene), and digested with BamHI as the insert for the second methioninase gene.

Ligation was performed with DNA Ligation Kit from Stratagene at higher T4 ligase concentration. See FIG. 3. The resulting plasmid was then transformed into competent *E. coli* BL2 1 (DE3) cells according to the instruction manual.

Positive clones were selected from ampicillin-containing plates. After optional storage at 4° C. overnight, the clones which expressed high levels of methioninase had a distinct yellow-orange color due to high enrichment of the pyridoxal phosphate-containing methioninase. The clone with the highest indication of methioninase content was confirmed by activity assay. When assayed for activity, all yellow-orange colonies were positive for methioninase and noncolored clones were methioninase negative. The clone with highest methioninase activity pAC-11 was selected and confirmed by BamHI and NdeI digestion.

pAC-11 provides methioninase production as high as 50% of the total intracellular protein as shown in Table 2.

TABLE 2

Expression and Stability of pAC-1 and pAC-11

|  | pAC-1 | pAC-11 |
|---|---|---|
| Specific activity of extract (units/mg): | 3 units/mg | 10 units/mg |
| Expression level (% of total protein): | 15% | 50% |
| Stability | Low | Stable |

EXAMPLE 4

Fermentation Of Recombinant Methioninase Expression Clones

Figure 4:
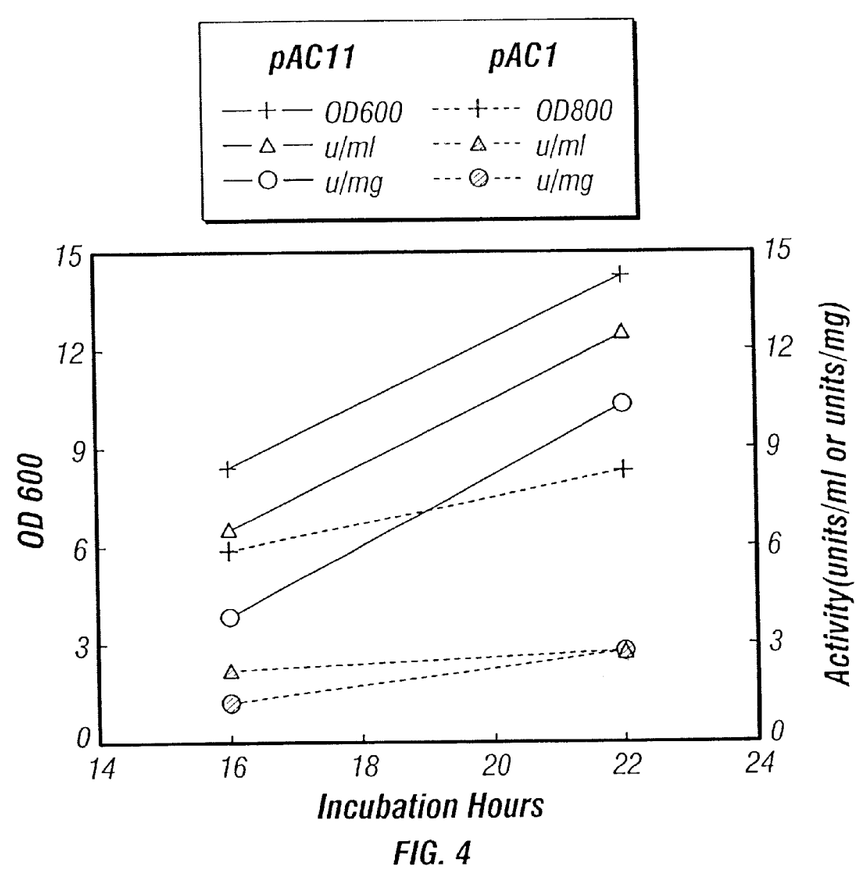
FIG. 4 compares methioninase expression levels as a function of time using single and two-copy expression systems.

Cells containing pAC-1 and pAC-11 were grown in Terrific Broth medium containing either ampicillin (100 μg/ml) or tetracycline (10 μg), at 28° C. or 37° C. with shaking. Table 3 compares the level of methioninase production obtained from these vectors; these results are graphed in FIG. 4 to show time course.

TABLE 3

Comparisons for PAC-1 and PAC-11 Clones

| | Growth** | OD 600 | | Activity | Specific Activity |
|---|---|---|---|---|---|
| Clone* | Hours | Total | Units/OD | Units/ml | Units/mg |
| pAC-1 | 16 | 5.8 | 0.38 | 2.2 | 1.2 |
|  | 22 | 8.2 | 0.34 | 2.8 | 2.8 |
| pAC-11 | 16 | 8.2 | 0.78 | 6.4 | 3.8 |
|  | 22 | 14.2 | 0.88 | 12.4 | 10.2 |

*pAC-1 clone contains one methioninase gene.
pAC-11 clone contains two methioninase genes.
**Bacteria growth in 1XTB 800 ml, at 28° C.

EXAMPLE 5

Purification of Recombinant Methioninase

An outline of the purification method is provided in FIG. 2.

(1) Pre-column Treatment of the Sample

The bacteria were harvested by centrifugation at 800×g at 4° C. for 10 min. The bacterial pellet is then suspended in extraction solution (20 mM potassium phosphate pH 9.0, 10 μM pyridoxal phosphate and 0.01% β-mercaptoethanol) and disrupted with a cavitator-type homogenizer (Microfluidics Corp. model # HC 8000). Heat treatment of the homogenate is then carried out at 50° C. for one minute. The suspension is centrifuged with an automatic refrigerated centrifuge (SORVALL Superspeed RC 2-B) at 4° C. at 13 k rpm for 30 min. The supernatant is then collected. This step is followed by ultrafiltration by a Milipore Prep/Scale—TFF PLHK 100k 2.5 ft² cartridge with buffer (10 mM potassium phosphate pH 8.3). The pH is adjusted to 7.2 by ultrafiltration.

(2) Chromatographic Conditions

The First Column: DEAE Sepharose FF

Column: XK 100/60, Height: 32 cm, Volume: 2.5 L

Solution: [A] 40 mM potassium chloride, 10 mM potassium phosphate (pH7.2) containing 10 μM pyridoxal phosphate and 0.01% β-mercaptoethanol.
[B] 200 mM potassium chloride, 10 mM potassium phosphate (PH7.2) containing 10 μM pyridoxal phosphate and 0.01% β-mercaptoethanol.

Flow Rate: 5 ml/min.

Sample: About 100–200 g of total protein (10–20 mg/ml) are applied on the first column.

Gradient: [1] Pre-wash with solution A approximately 10 volumes until the $OD_{280}$ drops below 0.1.
[2] Gradient: Solution B from 20%–100%.

Fractions: Elution fractions of 200 ml are collected. The fractions containing methioninase are identified by activity assay and pooled.

The Second Column: DEAE Sepharose FF

Column: XK 50/30, Height: 25 cm, Volume: 500 ml

Solution: [A] 100 mM potassium chloride, 10 mM potassium phosphate (pH 8.3) containing 10 μM pyridoxal phosphate and 0. 0 1% β-mercaptoethanol.
[B] 200 mM potassium chloride, 10 mM potassium phosphate (pH 8.3) containing 10 μM pyridoxal phosphate and 0.01% β-mercaptoethanol.

Flow Rate: 5 ml/min.

Sample: Approximately 10–20 g of total protein (2–4 mg/ml), after dialysis in 100 mM potassium chloride, 10 mM potassium phosphate (pH 8.3) containing 10 μM pyridoxal phosphate for 24 hours, are applied on the second column.

Gradient: [1] Pre-wash with solution A approximately 5 volumes until the $OD_{280}$ drops below 0.05.
[2] Gradient: Solution B from 0%–60%.

Fractions: Elution fractions of 200 ml are collected. The fractions containing methioninase are identified by the activity assay and pooled.

The Third Column: Sephacryl S-200 HR

Column: HiPrep 26/60, volume 320 ml.

Solution: 0.15 M sodium chloride in 10 mM sodium phosphate (pH7.2)

Flow Rate: 1.2 ml/min.

Sample: Approximately 10 ml concentrated sample. (after dialysis in 0.15 M sodium chloride, 10 mM sodium phosphate (pH7.2) for 12 hours), are applied to the third column.

Fractions: Elution fractions of 20 ml containing methioninase, which are identified by yellow color and activity assay, are collected.

The Fourth Column: ACTICLEAN® ETOX

Purified methioninase (10–20 mg protein/ml) in a volume of 100–200 ml is applied on a 500 ml ACTICLEAN® ETOX column, and eluted with elution buffer (0.15 M sodium chloride in 10 mM sodium phosphate pH7.2) in order to eliminate endotoxin. ACTICLEAN® ETOX is reusable and can be cleaned with 1 M sodium hydroxide and can be autoclaved.

Concentration of the Final Eluant

The final eluant is concentrate with 30 K Amicon Centriprep Concentrators. The formulation for purified methioninase is 0.15 M sodium chloride, 10 mM sodium phosphate, pH7.2.

Purification of Methioninase Histidine: Chromatography on $Ni^{++}$ Sepharose column The cell homogenate, after pre-column treatment, is suspended in binding buffer (5 mM imidazole, 0.5 M NaCl, 20 mM Tris, HCl, pH7.9). The column is then washed with 10 volumes of binding buffer followed by washes with 6 volumes of wash buffer (60 mM imidazole, 0.5 M sodium chloride, 20 mM Tris, HCl, pH7.9). Elution occurs after 6 volumes of elution buffer (1 M imidazole, 0.5 M NaCl, 20 mM Tris. HCl pH7.9) have been run through the column. The fractions containing methioninase, identified by yellow color, are collected.

What is claimed is:

1. A method to produce methioninase at high levels in *E. coli* which method comprises culturing *E. coli* cells which have been modified to contain a DNA molecule comprising an expression cassette comprising two or more tandem copies of a nucleotide sequence encoding methioninase which nucleotide sequence is selected from the group consisting of (a) a nucleotide sequence that encodes a protein having the amino acid sequence of SEQ ID NO: 7; and (b) a nucleotide sequence that is SEQ ID NO: 6; wherein methioninase is produced in *E. coli* at levels of about 40–75% of the total cellular protein.

2. The method of claim 1 wherein the promoter is a constitutive promoter.

3. The method of claim 2 wherein said promoter is a T7 RNA polymerase promoter.

4. The method of claim 3 wherein the *E coli* cells are BL21 (DE3) cells.

5. The method of claim 1 wherein the methioninase is produced intracellularly.

* * * * *

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gccggtctgt ggaataagct                    20

<210> SEQ ID NO 2

```
<211> LENGTH: 20
<212> TYPE: DNA
<213> ORGANISM: Artificial Sequence
<220> FEATURE:
<223> OTHER INFORMATION: Primer

<400> SEQUENCE: 2
ccagggtcga ctccagcgcc                                              20

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
ggaattccat atgcacggct ccaacaagc                                    29

<210> SEQ ID NO 4
<211> LENGTH: 51
<212> TYPE: DNA
<213> ORGANISM: Artificial Sequence
<220> FEATURE:
<223> OTHER INFORMATION: Primer

<400> SEQUENCE: 4
agtcatccta ggtcacatca tcatcatcat catggcactc gccttgagtg c           51

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
agtcatccta ggtcaggcac tcgccttgag tgc                               33

<210> SEQ ID NO 6
<211> LENGTH: 1369
<212> TYPE: DNA
<213> ORGANISM: P. putida
<220> FEATURE:
<221> NAME/KEY: CDS
<222> LOCATION: (48)...(1241)

<400> SEQUENCE: 6
gccggtctgt ggaataagct tataacaaac cacaagaggc ggttgcc atg cac ggc     56
                                                 Met His Gly
                                                   1 tcc aac aag ctc cca gga ttt gcc acc cgc gcc att cac cat ggc tac   104
Ser Asn Lys Leu Pro Gly Phe Ala Thr Arg Ala Ile His His Gly Tyr
  5                  10                  15 gac ccc cag gac cac ggc ggc gca ctg gtg cca ccg gtc tac cag acc   152
Asp Pro Gln Asp His Gly Gly Ala Leu Val Pro Pro Val Tyr Gln Thr
 20                  25                  30                  35 gcg acg ttc acc ttc ccc acc gtg gaa tac ggc gct gcg tgc ttt gcc   200
Ala Thr Phe Thr Phe Pro Thr Val Glu Tyr Gly Ala Ala Cys Phe Ala
                 40                  45                  50 ggc gag cag gcc ggc cat ttc tac agc cgc atc tcc aac ccc acc ctc   248
Gly Glu Gln Ala Gly His Phe Tyr Ser Arg Ile Ser Asn Pro Thr Leu
             55                  60                  65 aac ctg ctg gaa gca cgc atg gcc tcg ctg gaa ggc ggc gag gcc ggg   296
Asn Leu Leu Glu Ala Arg Met Ala Ser Leu Glu Gly Gly Glu Ala Gly
```

```
                        70                  75                  80
ctg gcg ctg gcc tcg ggc atg ggg gcg atc acg tcc acg cta tgg aca        344
Leu Ala Leu Ala Ser Gly Met Gly Ala Ile Thr Ser Thr Leu Trp Thr
         85                  90                  95 ctg ctg cgc ccc ggt gac gag gtg ctg ctg ggc aac acc ctg tac ggc        392
Leu Leu Arg Pro Gly Asp Glu Val Leu Leu Gly Asn Thr Leu Tyr Gly
100                 105                 110                 115 tgc acc ttt gcc ttc ctg cac cac ggc atc ggc gag ttc ggg gtc aag        440
Cys Thr Phe Ala Phe Leu His His Gly Ile Gly Glu Phe Gly Val Lys
                120                 125                 130 ctg cgc cat gtg gac atg gcc gac ctg cag gca ctg gag gcg gcc atg        488
Leu Arg His Val Asp Met Ala Asp Leu Gln Ala Leu Glu Ala Ala Met
                135                 140                 145 acg ccg gcc acc cgg gtg atc tat ttc gag tcg ccg gcc aac ccc aac        536
Thr Pro Ala Thr Arg Val Ile Tyr Phe Glu Ser Pro Ala Asn Pro Asn
            150                 155                 160 atg cac atg gcc gat atc gcc ggc gtg gcg aag att gca cgc aag cac        584
Met His Met Ala Asp Ile Ala Gly Val Ala Lys Ile Ala Arg Lys His
        165                 170                 175 ggc gcg acc gtg gtg gtc gac aac acc tac tgc acg ccg tac ctg caa        632
Gly Ala Thr Val Val Val Asp Asn Thr Tyr Cys Thr Pro Tyr Leu Gln
180                 185                 190                 195 cgg cca ctg gag ctg ggc gcc gac ctg gtg gtg cat tcg gcc acc aag        680
Arg Pro Leu Glu Leu Gly Ala Asp Leu Val Val His Ser Ala Thr Lys
                200                 205                 210 tac ctg agc ggc cat ggc gac atc act gct ggc att gtg gtg ggc agc        728
Tyr Leu Ser Gly His Gly Asp Ile Thr Ala Gly Ile Val Val Gly Ser
                215                 220                 225 cag gca ctg gtg gac cgt ata cgt ctg cag ggc ctc aag gac atg acc        776
Gln Ala Leu Val Asp Arg Ile Arg Leu Gln Gly Leu Lys Asp Met Thr
                230                 235                 240 ggt gcg gtg ctc tcg ccc cat gac gcc gca ctg ttg atg cgc ggc atc        824
Gly Ala Val Leu Ser Pro His Asp Ala Ala Leu Leu Met Arg Gly Ile
            245                 250                 255 aag acc ctc aac ctg cgc atg gac cgc cac tgc gcc aac gct cag gtg        872
Lys Thr Leu Asn Leu Arg Met Asp Arg His Cys Ala Asn Ala Gln Val
260                 265                 270                 275 ctg gcc gag ttc ctc gcc cgg cag ccg cag gtg gag ctg atc cat tac        920
Leu Ala Glu Phe Leu Ala Arg Gln Pro Gln Val Glu Leu Ile His Tyr
                280                 285                 290 ccg ggc ctg gcg agc ttc ccg cag tac acc ctg gcc cgc cag cag atg        968
Pro Gly Leu Ala Ser Phe Pro Gln Tyr Thr Leu Ala Arg Gln Gln Met
                295                 300                 305 agc cag ccg ggc ggc atg atc gcc ttc gaa ctc aag ggc ggc atc ggt       1016
Ser Gln Pro Gly Gly Met Ile Ala Phe Glu Leu Lys Gly Gly Ile Gly
            310                 315                 320 gcc ggg cgg cgg ttc atg aac gcc ctg caa ctg ttc agc cgc gcg gtg       1064
Ala Gly Arg Arg Phe Met Asn Ala Leu Gln Leu Phe Ser Arg Ala Val
325                 330                 335 agc ctg ggc gat gcc gag tcg ctg gcg cag cac ccg gca agc atg act       1112
Ser Leu Gly Asp Ala Glu Ser Leu Ala Gln His Pro Ala Ser Met Thr
340                 345                 350                 355 cat tcc agc tat acc cca gag gag cgt gcg cat tac ggc atc tcc gag       1160
His Ser Ser Tyr Thr Pro Glu Glu Arg Ala His Tyr Gly Ile Ser Glu
                360                 365                 370 ggg ctg gtg cgg ttg tcg gtg ggg ctg gaa gac atc gac gac ctg ctg       1208
Gly Leu Val Arg Leu Ser Val Gly Leu Glu Asp Ile Asp Asp Leu Leu
                375                 380                 385 gcc gat gtg caa cag gca ctc aag gcg agt gcc tgaacccgtc acggatgagg    1261
Ala Asp Val Gln Gln Ala Leu Lys Ala Ser Ala
```

```
Ala Asp Val Gln Gln Ala Leu Lys Ala Ser Ala
        390                 395 tcaatgcaat ggtggcaatg atgaaccttg tgcctggcga cggcgtgccc ggtgacagcg      1321
accctggcga aactgcagag tggctggagg cgctggagtc gaccctgg                   1369

<210> SEQ ID NO 7
<211> LENGTH: 398
<212> TYPE: PRT
<213> ORGANISM: P. putida

<400> SEQUENCE: 7

Met His Gly Ser Asn Lys Leu Pro Gly Phe Ala Thr Arg Ala Ile His
1               5                   10                  15

His Gly Tyr Asp Pro Gln Asp His Gly Ala Leu Val Pro Val
            20                  25                  30

Tyr Gln Thr Ala Thr Phe Thr Phe Pro Thr Val Glu Tyr Gly Ala Ala
                35                  40                  45

Cys Phe Ala Gly Glu Gln Ala Gly His Phe Tyr Ser Arg Ile Ser Asn
    50                  55                  60

Pro Thr Leu Asn Leu Leu Glu Ala Arg Met Ala Ser Leu Glu Gly Gly
65                  70                  75                  80

Glu Ala Gly Leu Ala Leu Ala Ser Gly Met Gly Ala Ile Thr Ser Thr
                85                  90                  95

Leu Trp Thr Leu Leu Arg Pro Gly Asp Glu Val Leu Leu Gly Asn Thr
                100                 105                 110

Leu Tyr Gly Cys Thr Phe Ala Phe Leu His His Gly Ile Gly Glu Phe
            115                 120                 125

Gly Val Lys Leu Arg His Val Asp Met Ala Asp Leu Gln Ala Leu Glu
130                 135                 140

Ala Ala Met Thr Pro Ala Thr Arg Val Ile Tyr Phe Glu Ser Pro Ala
145                 150                 155                 160

Asn Pro Asn Met His Met Ala Asp Ile Ala Gly Val Ala Lys Ile Ala
                165                 170                 175

Arg Lys His Gly Ala Thr Val Val Asp Asn Thr Tyr Cys Thr Pro
            180                 185                 190

Tyr Leu Gln Arg Pro Leu Glu Leu Gly Ala Asp Leu Val Val His Ser
            195                 200                 205

Ala Thr Lys Tyr Leu Ser Gly His Gly Asp Ile Thr Ala Gly Ile Val
210                 215                 220

Val Gly Ser Gln Ala Leu Val Asp Arg Ile Arg Leu Gln Gly Leu Lys
225                 230                 235                 240

Asp Met Thr Gly Ala Val Leu Ser Pro His Asp Ala Ala Leu Leu Met
                245                 250                 255

Arg Gly Ile Lys Thr Leu Asn Leu Arg Met Asp Arg His Cys Ala Asn
                260                 265                 270

Ala Gln Val Leu Ala Glu Phe Leu Ala Arg Gln Pro Gln Val Glu Leu
            275                 280                 285

Ile His Tyr Pro Gly Leu Ala Ser Phe Pro Gln Tyr Thr Leu Ala Arg
    290                 295                 300

Gln Gln Met Ser Gln Pro Gly Gly Met Ile Ala Phe Glu Leu Lys Gly
305                 310                 315                 320

Gly Ile Gly Ala Gly Arg Arg Phe Met Asn Ala Leu Gln Leu Phe Ser
                325                 330                 335

Arg Ala Val Ser Leu Gly Asp Ala Glu Ser Leu Ala Gln His Pro Ala
```

```
                      -continued
              340              345              350
Ser Met Thr His Ser Ser Tyr Thr Pro Glu Glu Arg Ala His Tyr Gly
        355              360              365

Ile Ser Glu Gly Leu Val Arg Leu Ser Val Gly Leu Glu Asp Ile Asp
    370              375              380

Asp Leu Leu Ala Asp Val Gln Gln Ala Leu Lys Ala Ser Ala
385              390              395
```